United States Patent [19]

Stice

[11] Patent Number: 4,984,581
[45] Date of Patent: Jan. 15, 1991

[54] FLEXIBLE GUIDE HAVING TWO-WAY SHAPE MEMORY ALLOY

[75] Inventor: James D. Stice, Minneapolis, Minn.

[73] Assignee: Flexmedics Corporation, Minneapolis, Minn.

[21] Appl. No.: 256,658

[22] Filed: Oct. 12, 1988

[51] Int. Cl.⁵ .............................................. A61B 5/00
[52] U.S. Cl. .................................... 128/772; 128/657; 604/95; 604/164; 604/280
[58] Field of Search ................. 128/657, 772; 604/95, 604/164, 170, 280, 282

[56] References Cited

U.S. PATENT DOCUMENTS

| | | | |
|---|---|---|---|
| 3,452,742 | 7/1969 | Muller | 128/772 |
| 3,521,620 | 7/1970 | Cook | 128/772 |
| 3,528,406 | 9/1970 | Jeckel et al. | 128/772 |
| 3,547,103 | 12/1970 | Cook | 128/303 |
| 3,612,058 | 10/1971 | Ackerman | 128/772 |
| 3,625,200 | 12/1971 | Muller | 128/303 |
| 3,731,671 | 5/1973 | Mageoh | 128/772 |
| 3,749,086 | 7/1973 | Kline et al. | 128/772 |
| 3,789,841 | 2/1974 | Antoshkiw | 128/772 |
| 3,841,308 | 10/1974 | Tate | 128/772 |
| 3,890,977 | 6/1975 | Wilson | 128/419 P |
| 3,906,938 | 9/1976 | Fleischhacker | 128/772 |
| 3,973,556 | 8/1976 | Fleischhacker | 128/772 |
| 4,003,369 | 1/1977 | Heilman et al. | 128/772 |
| 4,020,829 | 5/1977 | Willson et al. | 128/772 |
| 4,080,706 | 3/1978 | Heilman et al. | 128/772 |
| 4,170,990 | 10/1979 | Baumgart et al. | 128/92 B |
| 4,215,703 | 8/1980 | Willson | 128/772 |
| 4,456,017 | 6/1984 | Miles | 128/772 |
| 4,534,363 | 8/1985 | Gold | 128/772 |
| 4,538,622 | 9/1985 | Samson et al. | 128/772 |
| 4,543,090 | 9/1985 | McCoy | 604/95 |
| 4,545,390 | 10/1985 | Leary | 128/772 |
| 4,548,206 | 10/1985 | Osborne | 128/772 |
| 4,554,929 | 11/1985 | Samson et al. | 128/772 |
| 4,601,705 | 7/1986 | McCoy | 604/95 |
| 4,619,274 | 10/1986 | Morrison | 128/772 |
| 4,665,906 | 5/1987 | Jervis | 128/92 YN |
| 4,758,222 | 7/1988 | McCoy | 604/95 |
| 4,776,844 | 10/1988 | Ueda | 604/95 |

FOREIGN PATENT DOCUMENTS 0141006  5/1985  European Pat. Off. ............. 128/772

OTHER PUBLICATIONS

"Deformation and Transition Behavior Associated with the R-Phase in TiNi Alloys", S. Miyazaki et al., Metallurgical Transactions A, vol. 17A, Jan. 1986.

"The Effect of Aging on the Spontaneous Shape Change and the All-Round Shape Memory Effect in Ni-Rich TiNi Alloy", T. Honma, Proceedings of The International Conference on Martensitic Transformations (1986), pp. 709–716, The Japan Institute of Metals.

Primary Examiner—Randall L. Green
Assistant Examiner—Randy Shay
Attorney, Agent, or Firm—James R. Haller; Gregory P. Kaihoi; Mary P. Bauman

[57] ABSTRACT

A medical guide wire for insertion into body channels for accessing specific inner body areas without major surgery. The guide wire comprises an elongated, flexible guide having a core of a shape memory alloy, the guide utilizing the two-way memory properties of the shape memory alloy to impart tip-deflecting and rotational movement to the guide wire in response to a controlled thermal stimulus.

12 Claims, 3 Drawing Sheets 4,984,581

FLEXIBLE GUIDE HAVING TWO-WAY SHAPE MEMORY ALLOY

FIELD OF THE INVENTION

The invention relates to elongated, flexible guide units used in medical procedures to gain access to specific inner areas of the body without major surgery.

BACKGROUND OF THE INVENTION

In order to gain access to specific inner areas of the body, often times elongated, flexible guide units are used to enter the body through a small opening and travel through parts of the body through convenient channels. Guide units may be passed into the body via peripheral blood vessels, the gastrointestinal tract, or the urinary tract. Guide units, often referred to as guide wires, are commercially available and are currently used in cardiology, gastroenterology, urology, and radiology. Guide wires, once in place, serve as guides for the introduction of additional medical instruments such as catheters.

To assist in threading a guide through a predetermined body channel such as an artery, the guide may include a generally flexible body portion which is resistant to kinking and a forward end portion of increased flexibility, the end portion terminating in a smoothly rounded tip. The body portion may include a core of stainless steel or other metal, the core being appropriately dimensioned in cross section to provide the desired degree of flexibility to the guide wire. A coating of plastic, a plastic tube, or the like may be applied over the surface of the core, if desired. In order to provide greater flexibility to the guide at its forward end, the forward end of the core may include a section of lesser diameter and hence, of greater flexibility. An elongated, flexible helically wound wire forming an elongated coil may be employed at the forward end of the guide wire and may extend throughout the length of the guide wire. The coil functions to make the guide wire tip flexible to facilitate the tip in being guided through body channels. A small plug, preferably integrally formed on the forward end of the core, provides an attachment for the wire coil. The core may terminate at a position spaced from the guide end to provide the guide end with increased flexibility.

Safety wires are commonly employed with guide wires to prevent the forward end of the guide from unintentionally becoming detached from the body of the guide wire when the guide is removed from a body channel. In some cases, the core provides the function of a safety wire.

SUMMARY OF THE INVENTION

The present invention relates to an elongated, flexible guide having a flexible metal core of a shape memory alloy, the core being shape changeable to facilitate maneuvering of the guide through body channels to access specific inner body areas. The guide of the invention utilizes the two way memory properties of shape memory alloys to precisely modify the shape of the guide wire tip.

In a preferred embodiment, the flexible metal core has a forward end portion of reduced diameter to provide greater flexibility to the guide wire tip.

The core preferably is formed of a shape memory alloy such as nitinol and provides tip deflecting and rotational movement to the guide wire to facilitate the steerability of the tip.

DETAILED DESCRIPTION OF THE PREFERRED EMBODIMENTS

Figure 1:
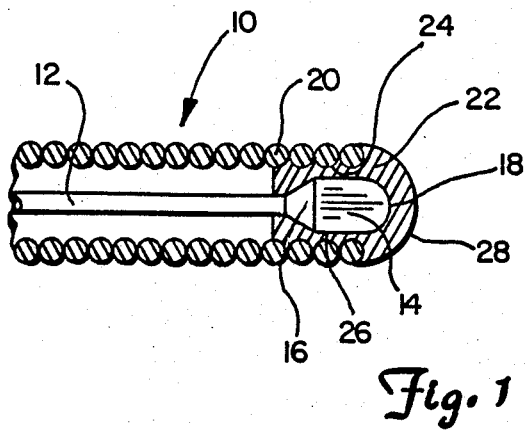
FIG. 1 is a broken-away cross-sectional view of an end portion of a guide of the invention.
Figure 2:
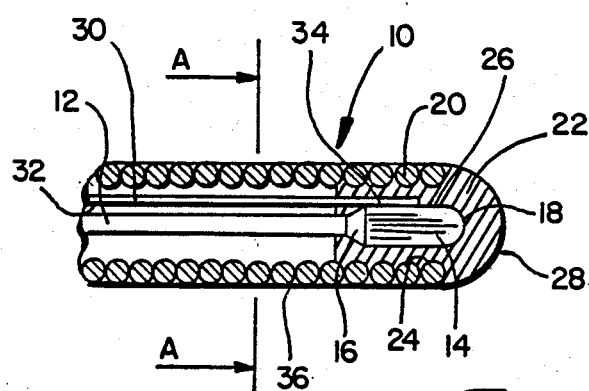
FIG. 2 is a broken-away cross-sectional view of an end portion of another embodiment of the invention.
Figure 3:
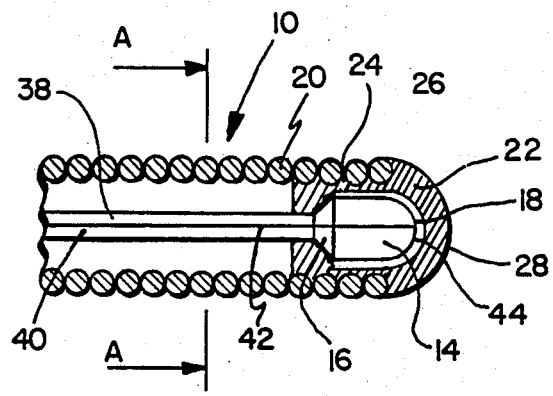
FIG. 3 is a broken-away cross-sectional view of an end portion of another embodiment of the invention.

FIG. 1 shows a guide wire 10 of the invention including, in a preferred embodiment, a core wire 12 having a forward end of reduced diameter and which terminates forwardly in a cylindrically shaped plug 14. The plug is generally circular in cross section, as desirably is the reduced diameter forward portion of the core 12. Desirably, as shown in FIGS. 1 and 2, the core and the plug are integrally formed, the plug representing an enlarged diameter portion of the core and the change in diameters forming a generally rearwardly facing annular shoulder 16 of the plug 14. The annular shoulder 16 may be in a plane generally perpendicular to the axis of the plug 14, or may be tapered as shown in FIGS. 1, 2 and 3 The forwardly facing end 18 of the plug 14 may be generally rounded as shown in FIG. 1. The guide wire of the invention incorporating a shape memory alloy core may be formed in any suitable guide wire configuration and is not limited to the designs shown in the figures.

In a preferred embodiment, the flexible forward portion of the guide includes an elongated, helically wound wire coil 20, the helically wound wire being of circular cross section as shown in the drawings or of any other convenient cross section such as a flattened cross section. The coil 20 may extend only through the flexible tip portion of the guide or alternately may extend the entire length of the guide. The coil may be formed of a metallic material such as stainless steel and is provided to lend flexibility to the forward tip of the guide and may also be used to provide a radiopaque guide tip which can be easily viewed by means of X-rays. In a preferred embodiment, the helical coil has an inner diameter at its forward (right hand) end that is only slightly larger or substantially equal to the outer diameter of the plug 14 such that the plug can be snugly received within the forward end of the coil to occupy the entire lumen of the coil. In some instances, it may be desirable to use a plastic tube in place of a helical coil to insulate the core of the guide wire from body tissue.

A bonding agent 22, such as an epoxy resin, is used to bond the plug 14 to the coil 20. As shown in FIG. 1, the bonding agent 22 extends between and bonds together confronting surfaces 24,26 of the core and plug, respectively. Desirably, the bonding agent extends within the coil rearwardly of the plug as shown in FIGS. 1, 2, 3, 5, and 6 and contacts the rearwardly facing annular shoulder 16 of the plug such that when the core is pulled rearwardly, to the left in FIG. 1, the bonding agent that extends rearwardly of the plug is placed under compressive stress. Since the plug and the forward portion of the coil are generally radially symmetrical and, accordingly when compressive tensile or shear forces are placed upon the bonding agent 22, they are circumferentially fairly evenly distributed, the bonding agent thus providing a strong bond between the coil and plug. Also, since the forward end of the core 12 and the plug 14 are integrally formed as shown in FIGS. 1 and 2, they are free of solder joints and the like which minimizes the possibility of the plug separating from the forward end of the core 12. The risk of separation of the plug and core is substantially reduced in this embodiment as compared to guide wires in which the forward end of the core or other safety wire is soldered or brazed to a forward plug.

As shown in the drawings, the bonding agent 22 extends forwardly of the plug 14 and provides the guide wire 10 with a generally hemispherical forward tip 28. The bonding agent may be a solder which is used to solder or braze the plug to the coil end, the solder functioning to strongly adhere the confronting surfaces 24,26 of the coil and plug, respectively. The bonding agent preferably is polymeric, and may be a hardenable resin such as an epoxy resin. The bonding agent 22 preferably extends rearwardly for only a few turns of the coil, as shown in the figures The forward tip 28 of the guide wire 10 and the rearward bonding agent 22 may be of the same material or of different materials so that the tip 28 may be formed of a harder metallic material or the like extending forwardly of the forward most turn of the helical coil and the remainder of the bonding material may be formed of a polymeric binder such as epoxy resin. In a preferred embodiment, the tip 28 and the bonding agent 22 are of the same material. Commercially available epoxy resins, which harden upon cure, are preferred bonding agents.

The core wire 12 employed in guides of the invention desirably is fabricated of a shape memory alloy which exhibits superelastic/pseudoelastic shape recovery characteristics. Shape memory alloys are characterized by their ability to modify their crystal structure and therefore their shape in response to a thermal stimulus. The alternate crystal structures provide the alloy with superelastic or pseudoelastic properties. A particularly preferred alloy is nitinol, an alloy of nickel and titanium, that is commercially available. The nitinol alloy is preferred because of its biocompatibility properties, making it particularly suited for human applications. Shape memory alloys such as nitinol are further preferred because of their capacity to elastically recover almost completely an initial configuration. Shape memory alloys have the capacity to avoid taking on a "set" when deformed so that a guide wire of the invention having a core of shape memory alloy may be substantially straight when unstressed, may deform as it is moved through curved body channels, and yet will recover its straight configuration when the stress is removed. Shape memory alloys in general, and nitinol in particular, can be soldered or brazed only with some difficulty and the solder joint that results is not of great strength. Therefore, the formation of an integral plug at the end of a core wire or safety wire as is used in the present invention avoids the necessity of soldering or otherwise attaching the end of a wire to a plug. The plug is in this way more resistant to being pulled from the end of a core or safety wire.

FIG. 2 shows the forward end portion of another guide wire of the invention similar to that shown in FIG. 1. The guide of FIG. 2 includes an elongated helical coil 20, and may optionally include an outer polymeric coating 36 of polytetrafluoroethylene or other polymeric material as can any other embodiments of the guide wire. The helical coil 20 may extend only through the end length of the guide or may extend the entire length of the guide, as desired. The forward end portion 12 of the core is illustrated as being rounded, but it may alternatively be shaped so as to taper forwardly as well.

Figure 2A:
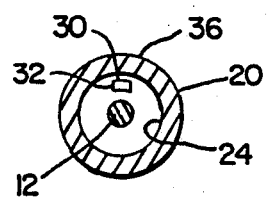
FIG. 2A is a cross-sectional view taken along line A—A of FIG. 2.

The guide wire of FIG. 2 further includes an electrically conductive element 30, such as a wire, extending along the length of the guide wire which is electrically connected to the plug 14 o the forward portion of the core wire by means of an electrically conductive adhesive means 34 such as an electrically conductive cement. The electrically conductive element 30 may alternatively be electrically connected to the core wire 12 at any desired location. The electrically conductive element 30 is preferably spaced from and electrically isolated from the core 12 by means of an insulating material such as the insulating coating 32. In a preferred embodiment, the electrically conductive element 30 comprises an electrically insulated wire. The cross sectional drawing of FIG. 2A shows the electrically conductive element 30 and its spaced relationship with the core wire 12. It should be understood that the electrically conductive element 30 may be of any desirable cross sectional shape and is not limited to the shape of a wire having a circular cross section. The electrically conductive element 30 may have an arch shaped cross section, a rectangular cross section as shown in FIG. 2A, or any other suitable configuration.

Figure 3A:
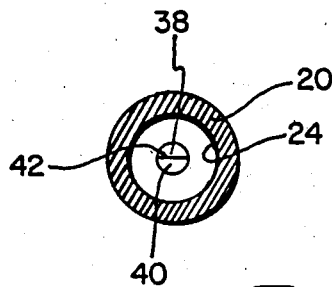
FIG. 3A is a cross sectional view taken along line A—A of FIG. 3.

Another alternative embodiment of the guide wire of the invention is shown in FIG. 3. This figure illustrates a guide wire having a core comprising first and second portions 38, 40, respectively, which are bonded together by a suitable adhesive such as an electrically insulating cement 42 to form a core wire. The first and second portions of the core 38, 40 may be insulated from the coil 20 as desired. The forward end of the core wire has a rapid increase in diameter to provide a plug 14 having a rearwardly facing annular shoulder 16. Preferably, the external surface of the plug 26 is coated with an electrically conducting material such as an electrically conducting cement 44 to electrically connect the first and second portions 38, 40, respectively, so that an electrical current can be conducted along one half of the guide wire to the plug 14 where it is transferred to the other half of the guide wire by means of the electrically conducting cement 44 and returned to an electrical power source via the other half of the core wire. Alternatively, any electrical connecting means may be used to electrically connect the two halves of the core at the forward end. Preferably, the bonding agent 22 used to bond the plug to the inner lumen of the coil 24 is an electrically insulating material such as an electrically insulating cement. A cross sectional view of the guide wire of FIG. 3 is shown in FIG. 3A.

Figure 4:
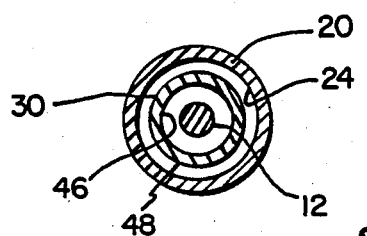
FIG. 4 is a cross sectional view of an alternative embodiment of the invention similar to that of FIG. 2A.

FIG. 4 illustrates an alternative embodiment of the guide wire of the invention wherein the electrically conductive element comprises an electrically conductive tube 30 having a circular cross section. In a preferred embodiment, the electrically conducting tube 30 is electrically isolated from the core 12 carried axially within its center by means of an insulating material such as an insulating coating 46 that may be carried either on the inner lumen of the electrically conductive tube 30 or on the external surface of the core 12. A second insulative coating 48 may be carried by the outer surface of the electrically conductive tube 30 to electrically isolate the same from the helical wire coil 20. In this embodiment, the electrically conductive tube 30 is preferably electrically connected to the plug 14 (shown in FIG. 2) by means of an electrically conductive adhesive material such as electrically conductive cement.

Figure 5:
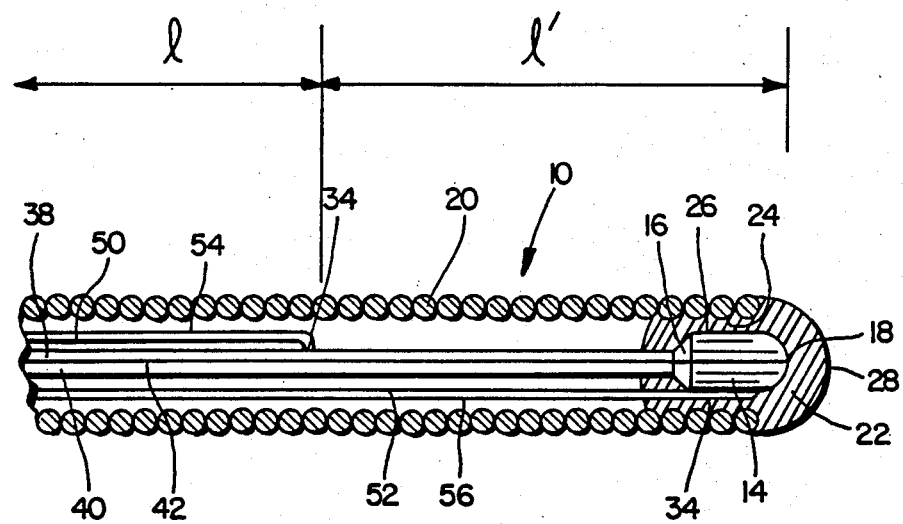
FIG. 5 is a broken away cross sectional view of an end portion of another embodiment of the invention.

FIG. 5 illustrates another embodiment of the guide wire of the invention similar to FIG. 3. The guide wire comprises a core having first and second halves 38, 40, respectively, the forward end of the core preferably terminating in a plug 14 having a larger diameter than the core, the difference in diameters defining an annular shoulder 16. The construction is similar to that of FIG. 3 which has been previously described. The guide wire of this embodiment ma additionally include an electrically conductive element such as the electrically conductive wire 50 which extends along a portion of the length of the core and is electrically connected to the first half 38 of the core at a point spaced from the forward end of the core upon which the plug 14 is carried. The electrically conductive wire 50 is electrically connected to the first half 38 of the core by means of an electrically conductive adhesive such as electrically conductive cement 34. Preferably, the electrically conductive element includes an insulating layer 54 to electrically isolate it from the core. Another electrically conductive element such as electrically conductive wire 52 extends along the length of the guide wire 10 and is electrically connected to the plug 14 or the core 40 at the forward end of the guide wire. Preferably, the electrically conductive wire 52 is electrically connected to the plug by means of an electrically conductive adhesive material such as electrically conductive cement 34. An electrically insulating material 56 is preferably carried by the wire 52 to electrically isolate the wire 52 from the core. Electrical insulating material could be carried by the core to electrically isolate the electrically conductive elements 50, 52 from the core. The two halves of the core 38, 40 are electrically isolated from one another by an electrically insulative material such as electrically insulative cement 42 and 22.

The guide wire of the invention utilizes a core desirably fabricated from a shape memory alloy such as nitinol to provide tip-deflecting and rotational movement of the guide wire forward tip. The guide wire of the present invention may exhibit both tip-deflecting movement and rotational movement effected by controlled temperature variation of the nitinol core wire. Rotational motion of the guide wire tip caused by controlled rotation of the shape memory alloy core is desirable in applications where the torqueability of the wire is no sufficient to achieve the desired guide wire end movement. The same 2-way memory properties are sought for both rotational and tip-deflecting motions. It is desirable to have a guide wire possessing good pseudoelasticity characteristics, the mechanical property of full shape recovery after deformation.

The shape memory effect of shape memory alloys is the shape recovery process that occurs when the alloy is thermally heated or cooled. One way memory is exhibited when a shape memory alloy is deformed from an original shape and then, upon heating, the alloy returns to the original shape. The behavior of shape memory alloy materials, which is based on a change in their structure, resides in that after deformation, the alloys will return to their original shape, the shape before the deformation takes place, after having been heated to above a certain temperature which is specific for the particular alloy involved. The temperature range in which the crystal structure of the alloy is spontaneously reversed, is called the conversion temperature range. A modification in the percentage composition or the addition of iron, cobalt, manganese, aluminum, silver or zirconium will produce a shift in the conversion temperature. The heat treatment applied to the shape memory alloy can also affect the shape memory properties of the alloy, and can be modified to obtain alloys with desired properties.

The shape memory alloys used in connection with the guide wire of the present invention should have a high resistance to electric current so that heat is produced when current is passed therethrough. The preferred electric current is RF frequency alternating current, which is not physiologically stimulating and would reduce the possibility of harm to a patient should there be any electric current leakage.

Two-way shape memory alloy properties can be achieved in which the shape memory alloy has a specific shape in one crystal structure and a specific different shape in another crystal structure. In a preferred embodiment, the shape memory alloy is changed from an austenitic structure to an R phase structure, the R phase being pseudoelastic giving the alloy excellent shape recovery properties. A martensitic structure can also be attained if desired. The austenitic structure shape is obtained by heating the shape memory alloy to a temperature above its specific temperature at which the conversion to an austenitic structure takes place. Once the shape memory alloy has taken on a shape in the austenitic state, the alloy may be cooled to a temperature below the temperature at which the formation of R-phase structures begin to take place to obtain an R-phase structure shape. This process produces the so called repeatable memory effect which constitutes a reversal of the original direction of movement of the alloy upon the change in temperature of the alloy. The guide is preferably operated at temperatures between 36° C. and 45° C. It is desirable not to exceed 45° C. on parts of the guide that contact body tissue because operating at higher temperatures could be destructive to body tissue. Some body proteins begin to break down at 45° C. In some embodiments, the sheath, or wire coil, may thermally insulate the core from body tissue enabling the temperature of the core to be raised above 45° C. while the sheath is at or below 45° C. This temperature gradient allows the core to be heated to a higher temperature which can decrease the response time of the guide wire shape change. This enables the user to receive a quicker shape change response which may be desirable in manipulating the guide.

In addition to the two-way memory exhibited by the tip, it thermal stimulus. The R-phase structure shape is preferred due to the pseudoelasticity and shape recovery properties of alloys in this phase. If the martensite phase is achieved on cooling, the tip will be "ductile" and will exhibit poor shape recovery characteristics. Also, there should be very little hysteresis in the shape change due to the small temperature change allowed by physiological constraints, again using the martensitic phase imposes problems due to its relatively large hysteresis of 10°-20° C. The use of two-way memory and the martensite phases has been previously disclosed in U.S. Pat. No. 4,170,990, describing two-way memory medical devices to connect tissue.

The R-phase structure of the NiTi alloy has favorable two way memory properties with a very small hysteresis (less than 5° C.). Thus, the austenite (beta) to R-phase transition is preferred for the shape memory element, rather than the beta to martensite transition.

In operation, the forward end of the guide wire is inserted into a body cavity such as a blood vessel while the core of the guide wire is approximately straight. A straight or nearly straight configuration, for example, may be the R-phase structure for that particular alloy. The guide wire is pushed through the cavity until it reaches a desired branch extending from the cavity. At this point, a control device may be manipulated to apply an electrical current to one or more portions of the guide wire to move the wire to a desired shape. Because of the high resistance of the shape memory alloy, heat is generated. When the temperature of the shape memory alloy is changed, the shape of the guide wire will change as the alloy attains a predetermined phase structure. In this manner, the forward end of the guide wire may be deflected into or toward one of the desired branches of the cavity. Once the forward end of the guide wire is in the branch, electrical current can be removed as desired from the memory element to allow it to cool. When it is desirable to move the shape memory alloy into its R-phase structure shape, a straight configuration for this example, the shape memory alloy is cooled to below its R-phase transitional temperature which will cause the shape memory alloy to assume its R-phase structure shape. It will be understood that the shape of the alloy core may be slowly and precisely changed in response to a precisely controlled thermal stimulus, in this case being electrical resistance heating.

These same two-way shape memory alloy properties used for tip-deflecting movement can be incorporated in the guide wire to attain rotational properties also. For example, the shape memory alloy core of the guide wire of the present invention can be formed with a straight axially aligned R-phase structure shape, and possess a rotationally twisted austenitic structure shape, the twist occurring about the axis of the core. In this configuration, the temperature of the shape memory alloy can be modified to change its phase and, therefore, its shape which will cause the shape memory alloy and thus the guide wire to twist radially about its axis, thus enabling reversible rotational movement of the guide wire tip. The tip can be manipulated in this manner by supplying an electric current to the twist shape portion of the shape memory alloy as desired to rotate the tip a desirable radial amount. The rotational movement and the tip-deflecting movement of the guide wire tip can be selectively employed as desired both in combination or separately.

Referring now to FIG. 1, the guide wire core 12 may be of a two-way shape memory alloy, thus enabling a current to be passed through the core 12, the plug 14 and the electrically conducting cement 22 to thus be returned through surrounding body tissue to the supply to complete the circuit. The core 12 can be heated and cooled as desired to assume a desired shape for facilitating steerability of the guide wire tip.

The guide wire tip configuration of FIG. 2 utilizes an electrically insulative cement 22 to insulate the tip from transferring electric current to body tissue. In the guide wire of FIG. 2, electrical current is passed through the core 12, the plug 14 and through electrically conducting cement 34 to the electrically conductive wire 30 in order to modify the temperature of the shape memory alloy core 12. Preferably, the core 12 and the electrically conductive wire 30 are both insulated so as to not conduct electrical current to the helical coil 20.

In the alternative embodiment of the guide wire tip shown in FIG. 3, electrical current is passed through one of the core halves such as half 38, through the electrically conductive cement 44 and returned to the power supply via the other half of the core 40. In this way, the core can be selectively heated and cooled to attain the desired tip movement. Any of these guide wire tip embodiments may have portions of the core shaped for use in attaining rotational movement and other portions of the core shaped for tip-deflecting movement.

FIG. 5 shows an alternative embodiment of the guide wire tip wherein a portion of the core L may be shaped for rotational movement of the tip, and the portion of the core spanning the distance L' may be shaped for tip-deflecting movement of the guide wire tip. In this embodiment, rotational movement of the guide wire tip may be obtained by passing electrical current through the electrically conducting wire 50 to the first half 38 of the core, thus completing an electrical circuit. Tip-deflecting movement of the guide wire tip may be attained by passing electrical current through the electrically conducting wire 52, the plug 14 and the second half of the core 40 to complete a tip-deflecting electrical circuit. Other electrical circuits may be employed as desired.

Figure 6:
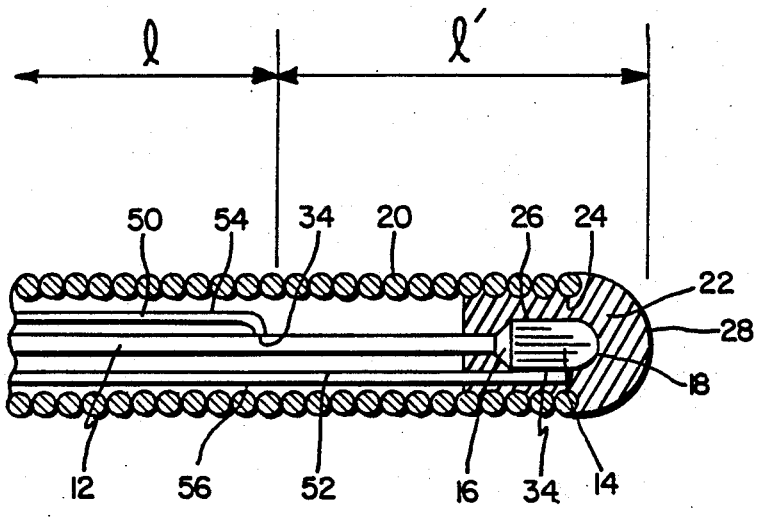
FIG. 6 is a broken away cross sectional view of an end portion of another embodiment of the invention.

FIG. 6 shows an alternative embodiment of the guide wire of the invention, the guide wire having a core 12 with an integrally connected, larger diameter plug 14. This embodiment of the invention employs an electrically conductive wire 52 electrically connected to the plug 14 by means of an electrically conductive cement 34. Preferably, the wire 52 is electrically isolated from the core 12 and the coil 20 by means of insulative material such as wire insulation 56. This embodiment also employs a wire 50 electrically connected to the core 12 at a location spaced from the forward end plug 14 of the core 12. The wire 50 is preferably electrically connected to the core 12 by means of an electrically conductive cement 34. The wire 50 is preferably electrically isolated from the coil 20 and the core 12 by insulation means such as that of wire insulation 54. Preferably, the bonding agent 22 is of an insulative material to avoid conducting electrical current to body tissue in use.

FIG. 6 displays the guide wire tip having both rotational movement and tip deflecting movement facilitated by a shape memory alloy core. In the embodiment of FIG. 6, the portion of the core of the guide wire labeled L is configured for rotational motion of the tip and the portion of the core labeled L' is configured for tip-deflecting movement of the guide wire tip. Other configurations may be used as desired. In order to exhibit both rotational and tip-deflecting movement of the guide wire tip, an electrical current is passed through the wire 52, the electrically conductive cement 34, the plug 14 and the core 12 to complete an electrical circuit with a power supply and an electrical control means. In order to engage rotational motion of the guide wire tip, a current is passed through electrically conductive wire 50 which is electrically connected to the core 12 by means of electrically conductive cement 34 to complete an electrical circuit. Tip deflecting movement of the guide wire tip is provided by passing electrical current through the wire 50, the portion L' of the core 12, the plug 14 and the wire 52 connected to the plug by means of electrically conductive cement 34. In this configuration, and in other alternative configurations a will become apparent to those skilled in the art, rotational motion and tip deflecting motion can selectively be engaged independently of one another or at the same time. The amount of rotational movement or tip-deflecting movement may be controlled by controlling the amount of electrical current supplied to the guide wire core 12. Desirably, a control means is provided in combination with a power supply to selectively and precisely control the amount of current supplied to the guide wire core. The tip deflecting and rotational movement of the guide wire tip as shown in the present invention may be actuated using a fluid flush means of thermal actuation, by embodying an electrical resistance heating element adjacent the core of the guide, or by any other common heating method. The teachings of the present invention may be employed by many guide wire designs and are not limited to the designs shown in the drawings.

While a preferred embodiment of the present invention has been described, it should be understood that various changes, adaptations and modifications may be made therein without departing from the spirit of the invention and the scope of the appended claims.

What is claimed is:

1. A guidewire comprising an elongated, flexible core of a shape memory alloy which is changeable between a pseudoelastic austenitic phase structure and a pseudoelastic R-phase structure, the austenitic and R-phase structures having different predetermined corresponding core shapes, the core being selectively changeable between said phase structures in response to a thermal stimulus to impart tip-deflecting movement to the guidewire.

2. The guide wire of claim 1 wherein the core is selectively changeable between phases in response to a thermal stimulus to impart rotational movement to the guide wire.

3. The guide wire of claim 1 wherein the core is formed of Niti alloy.

4. The guide wire of claim 1 including a distal sheath comprising an elongated, helically wound wire coil providing a flexible tip, the core extending forwardly within the tip and terminating forwardly in an enlarged diameter portion of generally circular cross section and defining a plug carried adjacent the forward end of the coil, the plug being substantially radially symmetrical with respect to the coil, and an electrically conductive bonding agent bonding the plug to the coil to permit electrical current supplied to the core to travel through the core and the plug and into surrounding body tissue, the shape memory alloy core having an electrically resistive forward portion capable of R phase/austenitic phase transformation in response to an increased temperature resulting from application of an electric current to the core.

5. The guide wire of claim 1 including a forward flexible sheath comprising an elongated, helically wound wire coil providing a flexible tip, the core extending forwardly within the tip and terminating forwardly in an integral enlarged diameter portion of generally circular cross section and defining a plug carried adjacent the forward end of the coil, the plug being substantially radially symmetrical with respect to the coil, an electrically insulative bonding agent bonding the plug to the coil, and an elongated, electrically conductive element extending along the length of the guide wire electrically connected to the plug, the element being electrically isolated from the core, the core having an electrically resistive forward portion capable of R-phase/austenitic phase transformation in response to an increased temperature resulting from application of an electric current to the core.

6. The guide wire of claim 5 including a second elongated, electrically conductive element extending along a portion of the length of the core and electrically connected to the core at a position spaced from the plug, the core having an electrically resistive forward portion capable of R-phase/austenitic phase transformation in response to an increased temperature resulting from application of an electric current to the core.

7. The guide wire of claim 1 comprising an elongated, flexible core having first and second longitudinally separate, electrically isolated halves, the core terminating forwardly in an integral enlarged diameter portion of generally circular cross section defining first and second halves of a plug. The two halves of the plug being connected by an electrically conductive adhesive. A forward flexible sheath comprising an elongated, helically wound wire coil providing a flexible tip, the plug carried adjacent the forward end of the coil, the plug being substantially radially symmetrical with respect to the coil, and an electrically insulative bonding agent bonding the plug to the coil, the core having an electrically resistive forward portion capable of R phase/austenitic phase transformation in response to an increased temperature resulting from application of an electric current to the core.

8. The guide wire of claim 1 wherein said elongated, flexible central core has first and second longitudinally separate, electrically isolated halves, the first half of the core terminating forwardly in an integral enlarged diameter portion of generally circular cross section defining a first half of a plug, the second half of the core terminating in a forward end defining a second half of a plug, a forward flexible sheath comprising an elongated, helically wound wire coil providing a flexible tip, an electrically insulative bonding agent bonding the plug to the coil, a first electrically conductive element extending along the length of the guide wire electrically connected to the second half of the plug, the element being electrically isolated from the core, and a second electrically conductive element extending along a portion of the length of the guide wire electrically connected to the first half of the core at a position spaced from the plug, the second element being electrically isolated from the core, the core having an electrically resistive forward portion capable of R phase/austenitic phase transformation in response to an increased temperature resulting from application of an electric current to the core.

9. The guidewire of claim 1 wherein said pseudoelastic R-phase structure core shape is stable at body temperature and conversion to said pseudoelastic austenitic phase structure core shape is substantially complete at 45° C.

10. The guidewire of claim 1 wherein said pseudoelastic R-phase structure is substantially stable at approximately 36° C. and conversion to said pseudoelastic austenitic phase structure core shape is substantially complete at approximately 45° C.

11. A guidewire comprising an elongated, flexible core of a two-way shape memory alloy which is selectively changeable in response to a thermal stimulus between a first phase wherein the core has a first configuration and a second phase wherein the core has a second configuration; an elongated, helically wound wire coil providing a flexible tip; the core extending forwardly within the tip and terminating forwardly in an enlarged diameter portion defining a plug carried adjacent the forward end of the coil; the position of the plug in the core's second configuration being angularly or rotationally displaced from the position of the tip in the core's first configuration.

12. The guide wire of claim 11 wherein the core is formed of a NiTi alloy.

* * * * *